United States Patent [19]

Umezawa, deceased et al.

[11] Patent Number: 4,877,870

[45] Date of Patent: Oct. 31, 1989

[54] PROCESS FOR PRODUCING 10-HYDROXYANTHRACYCLINES

[75] Inventors: Hamao Umezawa, deceased, late of Tokyo, by Kazuo Umezawa, heir; Kuniaki Tatsuta, Tokyo; Hiroyuki Kawai; Shohachi Nakajima, both of Maebashi, all of Japan

[73] Assignee: Kirin Beer Kabushiki Kaisha, Tokyo, Japan

[21] Appl. No.: 68,630

[22] Filed: Jun. 30, 1987

[30] Foreign Application Priority Data

Jul. 4, 1986 [JP] Japan ................................ 61-157358

[51] Int. Cl.$^4$ ........................ C07H 15/24; C07C 49/66
[52] U.S. Cl. ....................................... 536/6.4; 552/201
[58] Field of Search .......................... 536/6.4; 260/365

[56] References Cited

U.S. PATENT DOCUMENTS

| | | | |
|---|---|---|---|
| 4,045,498 | 8/1977 | Deno | 260/404 |
| 4,457,920 | 7/1984 | Mrozik | 536/7.1 |
| 4,617,146 | 10/1986 | Helmlinger et al. | 568/374 |

*Primary Examiner*—Ronald W. Griffin
*Assistant Examiner*—Elli Peselev
*Attorney, Agent, or Firm*—Ladas & Parry

[57] ABSTRACT

Disclosed is a process for producing a 10-hydroxyanthracycline of the following formula (II) which comprises reacting a compound of the following formula (I) or an acid addition salt thereof with an N-oxide of a tertiary amine

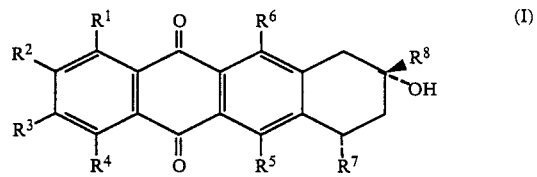

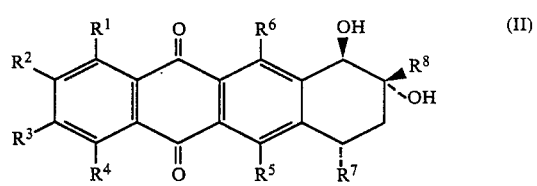

wherein: $R^1$ through $R^6$ each designate any of H, OH and $OCH_3$; $R^7$ designates any of H, OH and a sugar residue; and $R^8$ designates any of $C_2H_5$, $COCH_3$, $CH(OH)CH_3$, $CH(OH)CH_2(OH)$ and $COCH_2OH$. In accordance with this process, it is possible to efficiently introduce a hydroxyl group into the 10-position of an anthracycline having no substitutent at the same position thereof.

7 Claims, 12 Drawing Sheets

PROCESS FOR PRODUCING 10-HYDROXYANTHRACYCLINES

BACKGROUND OF THE INVENTION

The present invention relates to a process for producing 10-hydroxyanthracyclines stereospecifically from anthracyclines having no substituent at the 10-position thereof.

Specific examples of 10-hydroxyanthracyclines are betaclamycin (Journal of Antibiotics, 37, 935–938 (1984)) and 3'-deamino-3'-(4-morpholinyl)-13-deoxo-10-hydroxycarminomycin (hereinafter referred to as M-R20X2) (Japanese Patent Appln. No. 7196/1985). These are useful compounds which have antitumor activity. For example, betaclamycin inhibits proliferation of cultivated mouse leukemia cells (L1210) more effectively than aclacinomycin which has no substituent at the 10-position thereof. This betaclamycin has threfore drawn much attention. Furthermore, M-R20X2 also has remarkably high antitumor activity in comparison with 3'-deamino-3'-(4-morpholinyl)-13-deoxocarminomycin (hereinafter referred to as M-R20X) which differs from the M-R20X2 only in having no substituent (hydroxyl group) at the 10-position thereof. The comparative data will be shown hereinlater.

Accordingly, if an efficient method for introducing a hydroxyl group into the 10-position of an anthracycline having no substituent at the same position is developed, M-R20X can be readily converted into M-R20X2 which has higher antitumor activity while at the same time the antitumor activity of an anthracycline having no substituent at the 10-position thereof (e.g., adriamycin and daunomycin) can be expected to be enhanced by introducing a hydroxyl group into the same position.

The betaclamycin and M-R20X2 mentioned above, both having three asymmetric carbon atoms in the aglycon moiety thereof (7-, 9- and 10-position), are known to have the configurations 7S, 9R and 10R (Pharmazie, 39, 176–180(1984)).

Examples of organochemical approaches to the hydroxylation at 10-position include a process wherein a 9–10 epoxide is formed in an anthracyclinone having an olefin portion at the 9–10 position with the use of an organic peracid and the epoxide is subjected to ring cleavage to obtain a diastereomer mixture in a ratio of 9:1 (antidiol:syndiol) (A. S. Kende et al., J. Chem. Soc. Chem. Commun., 140 (1977)) and a process wherein a 10-ketoanthracycline is reduced to obtain a (10R) diastereomer and a (10S) diastereomer (the ratio of the (10R) diastereomer to the (10S) diastereomer obtained being 4:1) (H. Nakagawa et al., Tetradron Letters, 25, 31, 3355 (1984)).

The compounds obtained by these processes are mixtures of (10R) diastereomer and (10S) diastereomer and ordinarily have widely different antitumor activities. For this reason, these processes are accompanied by a problem in that the isomers except the desired compound which has the 7S, 9R and 10R configurations must be separated and removed. The former process further entails the problem of its inapplicability to glycosides.

SUMMARY OF THE INVENTION

The present invention has solved the above problems and provides a process for producing 10-hydroxyanthracyclines stereospecifically.

More particularly, the process for producing a 10-hydroxyanthracycline of the following formula (II) according to this invention comprises reacting a compound of the following formula (I) or an acid addition salt thereof with an N-oxide of a tertiary amine

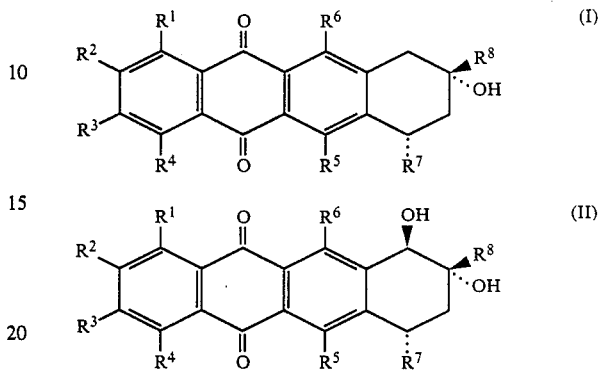

wherein: $R^1$ through $R^6$ each designate any of H, OH and $OCH_3$; $R^7$ designates any of H, OH and a sugar residue; and $R^8$ designates any of $C_2H_5$, $COCH_3$, $CH(OH)CH_3$, $CH(OH)CH_2(OH)$ and $COCH_2OH$.

DETAILED DESCRIPTION OF THE INVENTION

Figure 1:
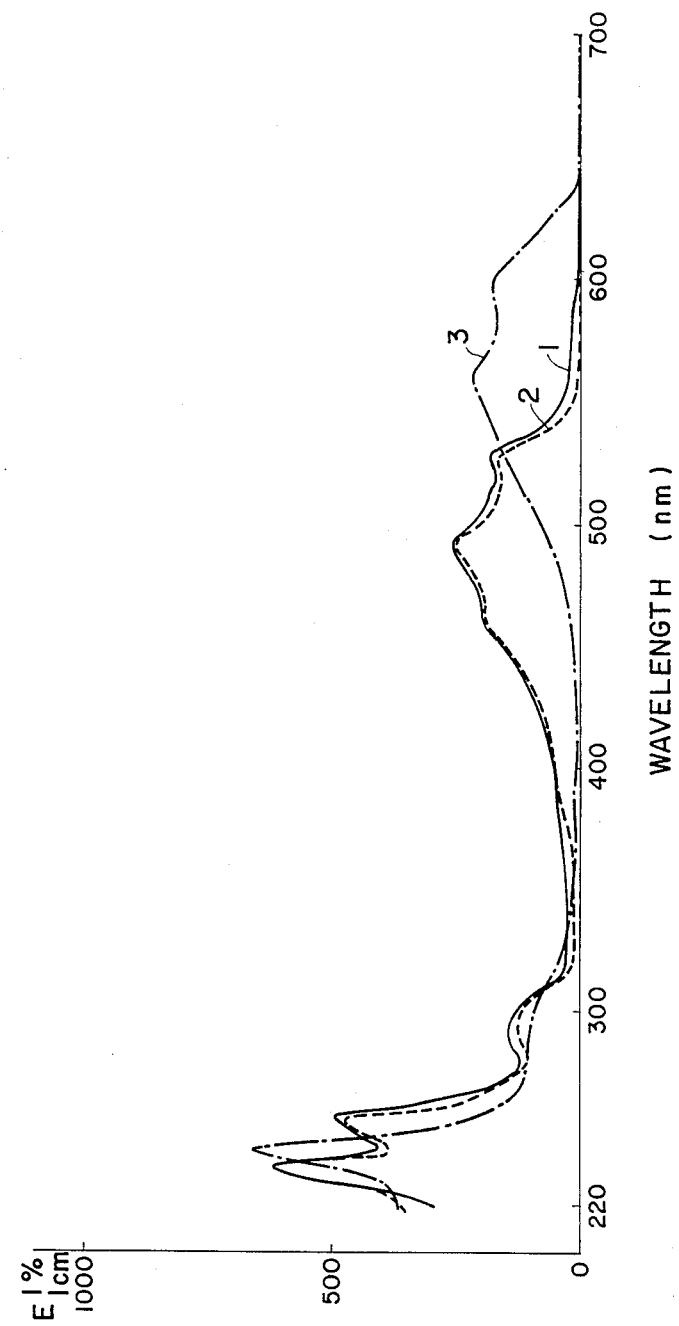
FIG. 1 is a graph showing the ultraviolet and visible absorption spectra of R20X, the curve 1 showing the spectrum in MeOH, the curve 2 the spectrum in 0.1N HCl-MeOH, and the curve 3 the spectrum in 0.1N NaOH-MeOH.

Anthracycline having no substituent at the 10-position thereof

The anthracycline into which a hydroxyl group is to be introduced stereoselectively at the 10-position thereof is a compound of the formula (I) shown hereinbefore or an acid addition salt thereof.

Specific examples of the sugar residues designated by the substituent $R^7$ are as follows:

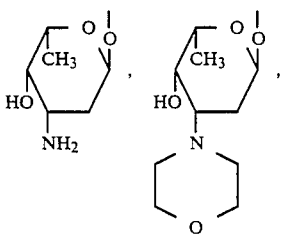

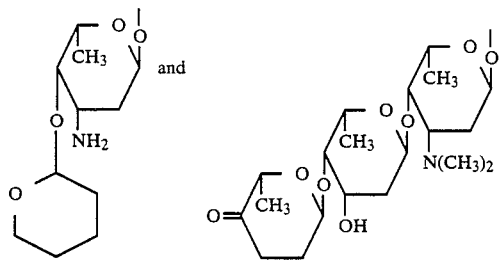

Examples of such compounds are adriamycin, daunomycin, aclacinomycin, THP-adriamycin, carminomycin, and M-R20X while examples of acid addition salts of these compounds are inorganic acid salts with hydrochloric acid, sulfuric acid and phosphoric acid or organic acid salts with acetic acid, lactic acid, propionic acid, maleic acid, oleic acid, palmitic acid, citric acid, succinic acid, tartaric acid, fumaric acid, glutamic acid, pantothenic acid and laurylsulfonic acid.

N-Oxide of a tertiary amine

Specific examples of the N-oxide of a tertiary amine used in the present invention are N-oxides of alkylamines such as trimethylamine and triethylamine, N-methylmorpholin-N-oxide and hydrates thereof.

Reaction conditions

In the present invention, the reaction of a compound of the formula (I) or an acid addition salt thereof with an N-oxide of a tertiary amine is carried out under the following conditions.

The quantity of the N-oxide of a tertiary amine used is not critical, but, from the point of view of reaction efficiency, this compound can be used in a quantity of at least 0.1 mol, preferably 1 to 2 mols, per mol of the compound of the formula (I) or an acid addition salt thereof.

Ordinarily, this reaction is carried out in a solvent. Examples of preferred solvents are dimethylformamide, acetonitrile, acetone, and dimethyl sulfoxide.

The reaction temperature is not critical either, and the reaction can be carried out generally in the range of from the solidifying point to the boiling point of the solvent employed.

Under the above stated reaction conditions, the reaction of introducing a hydroxyl group into the 10-position of the anthracycline can be terminated within about several hours to several days.

The reaction of the tertiary amine oxide according to the present invention is typically carried out by feeding a separately prepared amine oxide to the reaction system. Since the amine oxide is a compound which can be formed by the oxidation of the base amine relatively easily, however, the reaction of the amine oxide according to this invention can also be conducted by forming the amine oxide from the base amine and, for example, air in situ in the reaction system.

The reaction mixture thus obtained can be purified to isolate the desired 10-hydroxyanthracycline by a known purification procedure employed in the preparation of anthracyclines, for example, chromatography using silica gel and the like.

In accordance with the present invention, a hydroxyl group has been found to be introduced into an anthracycline stereospecifically so that the asymmetric carbon atom at the 10-position thereof will be (10R) as will be apparent from the Examples described hereinlater, but the particulars of the reaction mechanism are so far unknown.

EXPERIMENTAL EXAMPLES

In the following examples, "%" is "w/v%".

Reference Example 1 (Production of R20X)

13-Deoxocarminomycin (R20X), as one example of the compounds of the formula (I), was prepared by the cultivation of a microorganism.

(1) Inoculum Preparation

The culture medium used was prepared by dissolving the following ingredients in 1 liter of water and adjusting the pH of the solution to 7.2.

| | |
|---|---|
| Polypeptone | 1% |
| Molasses | 1% |
| Meat extract | 1% |

100 ml of the medium thus prepared was sterilized in a 500-ml Erlenmeyer flask and inoculated with a loopful of spores collected from a slant culture of *Actinomadura roseoviolacea* strain R20. The inoculated medium was subjected to shake culture for 5 days at 27° C. on a rotary shaker (200 r.p.m.) to prepare an inoculum.

(2) Cultivation

A fermentation medium was prepared by dissolving the following ingredients in 1 liter of water and adjusting the pH of the resultant solution to 7.4.

| | |
|---|---|
| Glucose | 2.5% |
| Soybean meal | 1.5% |
| Dry yeast | 0.2% |
| Calcium carbonate (precipitated) | 0.4% |

25 liters of the fermentation medium was sterilized in a 50-l jar fermenter, and 3 vials of the inoculums prepared as described above were added to the sterilized medium. Fermentation was carried out for 7 days at 27° C. at 1 v.v.m. and 200 r.p.m.

(3) Recovery of R20X

After the fermentation, the fermented mash was filtered to separate cells from the filtrate which was adjusted to pH 2 with 1N hydrochloric acid and adsorbed onto "Diaion HP20" (supplied by Mitsubishi Kasei K.K., Japan) packed in a 10×40 cm column. The substance thus adsorbed was washed with distilled water and 50% methanol and then eluted with methanol. The eluate was concentrated, and the concentrate was adjusted to pH 8.5 and extracted three times repeatedly with a chloroform-methanol (9:1) mixture. The extract was concentrated, and 6-fold volume of hexane was added thereto. The precipitate formed was dried to obtain 250 mg of a red powder (crude R20 substance product).

250 mg of this crude R20 substance product was dissolved in chloroform and applied to a 4×40 cm column packed with 250 g of silica gel equilibrated with chloroform. After the column was thoroughly washed with chloroform, the crude product was fractionated with a 10:1 chloroform-methanol mixture. Fractions thus obtained were concentrated to dryness under reduced pressure and developed on TLC ("Silica Gel 60", Merck & Co., Inc.) by using a 40:8:1:1 chloroform-methanol-acetic acid-water solvent system. The reddish orange band having a Rf value of approximately 0.3 was scraped off, and the fraction thus obtained was eluted, concentrated, and recrystallized from chloroform to yield 110 mg of R20X.

For reference, *Actinomadura roseoviolacea* strain R20 was deposited on July 5, 1983 with the Fermentation Research Institute, Agency of Industrial Science and Technology, where it was assigned the accession number FERM BP-945 (FERM P-7138), and the microbiological characteristics thereof are set forth in detail in Japanese Patent Laid-Open Pub. No. 38391/1985.

Reference Example 2 (Production of M-R20X)

M-R20X, which is a 3'-deamino-3'-(4-morpholinyl) derivative of the above mentioned R20X, as another example of the compounds of the formula (I), was prepared by the chemical reaction of R20X.

135 mg (0.27 mmol) of R20X was dissolved in 15 ml of chloroform. To the resulting solution were added 320 mg (2.66 mmol) of 2,2'-oxydiacetaldehyde and 17 mg (0.27 mmol) of sodium cyanoborohydride dissolved in a 1:1 acetonitrile-water solvent mixture to cause reaction at room temperature for one hour.

Upon completion of the reaction, the reaction solution was extracted three times with 50 ml of chloroform, and the chloroform solution was washed three times with 40 ml of water. The resulting chloroform solution was dried with sodium sulfate anhydride and then concentrated to dryness.

The crude product obtained was applied to silica gel ("Wakogel C-200", 10 g) column chromatography and eluted with a 200:1 chloroform-methanol solvent mixture to obtain the desired product. This product was further crystallized from a chloroform-hexane mixture to obtain 90 mg (58%) of the title compound.

EXAMPLE 1

40 mg of R20X was dissolved in 12 ml of DMF. To the resulting solution was added 16.8 mg of trimethylamine-N-oxide dihydrate, and the mixture obtained was stirred for 40 hours in air at room temperature. The reaction solution was then concentrated and applied to thin-layer silica gel chromatography using a 4:1 chloroform-methanol solvent system. A red band having an Rf value of 0.15 was scraped off and eluted with a chloroform-methanol solvent mixture, whereby 34.0 mg of 13-deoxo-10-hydroxycarminomycin (R20X2) was obtained.

The chemical shift values in the aglycone moiety of the $^{13}$C-NMR spectrum of R20X2 thus obtained, as compared with those of β-rhodomycin I, are shown in Table 1 below.

As is apparent from Table 1, the aglycone moieties of the two compounds were substantially identical.

The aglycone obtained by the acid hydrolysis of the R20X2 under ordinary conditions, for example, with 0.1N hydrochloric acid at 90° C. for 30 minutes, was found to have a specific rotatory power of $[\alpha]_D^{25} = +100°$ C. (C=0.42, in chloroform). The specific rotatory power of β-rhodomycinone, on the other hand, which is known to have the absolute configurations (7S, 9R, 10R), is $[\alpha]_D^{25} = +100°$ (C=0.27, in chloroform). Furthermore, the two compounds were substantially identical also in behavior when subjected to TLC and in other physicochemical properties.

The above data shows that the absolute configurations of the R20X2 obtained in accordance with the present invention are (7S, 9R, 10R) which are the same as those of β-rhodomycinone and that the reaction of the present invention proceeds stereospecifically.

TABLE 1

| | β-Rhodomycin I (in deuteromethanol) | R20X2 (in deuteromethanol) |
|---|---|---|
| 1 | 121.2 (ppm) | 121.3 (ppm) |
| 2 | 139.1 | 139.2 |
| 3 | 126.5 | 126.5 |
| 4 | 164.6 | 164.5 |
| 5 | 193.0 | 193.0 |
| 5a | 114.0 | 113.9 |
| 6 | 158.6 | 158.6 |
| 6a | 137.4 | 137.4 |
| 7 | 73.0 | 73.3 |
| 8 | 32.9 | 32.9 |
| 9 | 74.0 | 73.7 |
| 10 | 67.4 | 67.2 |
| 10a | 140.7 | 140.9 |
| 11 | 159.4 | 159.3 |
| 11a | 113.6 | 113.5 |
| 12 | 188.3 | 188.3 |
| 12a | 135.7 | 135.7 |
| 13 | 34.6 | 34.8 |
| 14 | 7.7 | 7.7 |

β-Rhodomycin I is represented by the following formula:

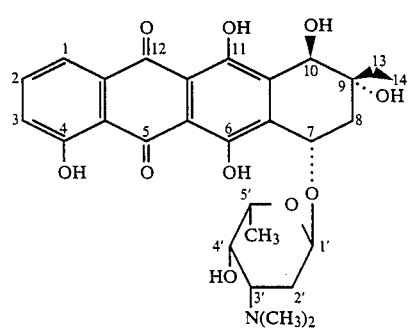

EXAMPLE 2

40 mg of M-R20X was dissolved in 12 ml of DMF. To the resulting solution was added 14.7 mg of trimethylamine-N-oxide dihydrate, and the mixture obtained was stirred for 40 hours in air at room temperature. The reaction solution was then concentrated and applied to thin-layer silica gel chromatography using a 10:1 chloroform-methanol solvent system. A band having an RF value of 0.42 was scraped off and eluted with a 10:1 chloroform-methanol solvent mixture, whereby 32.7 mg of M-R20X2 was obtained.

Figure 2:
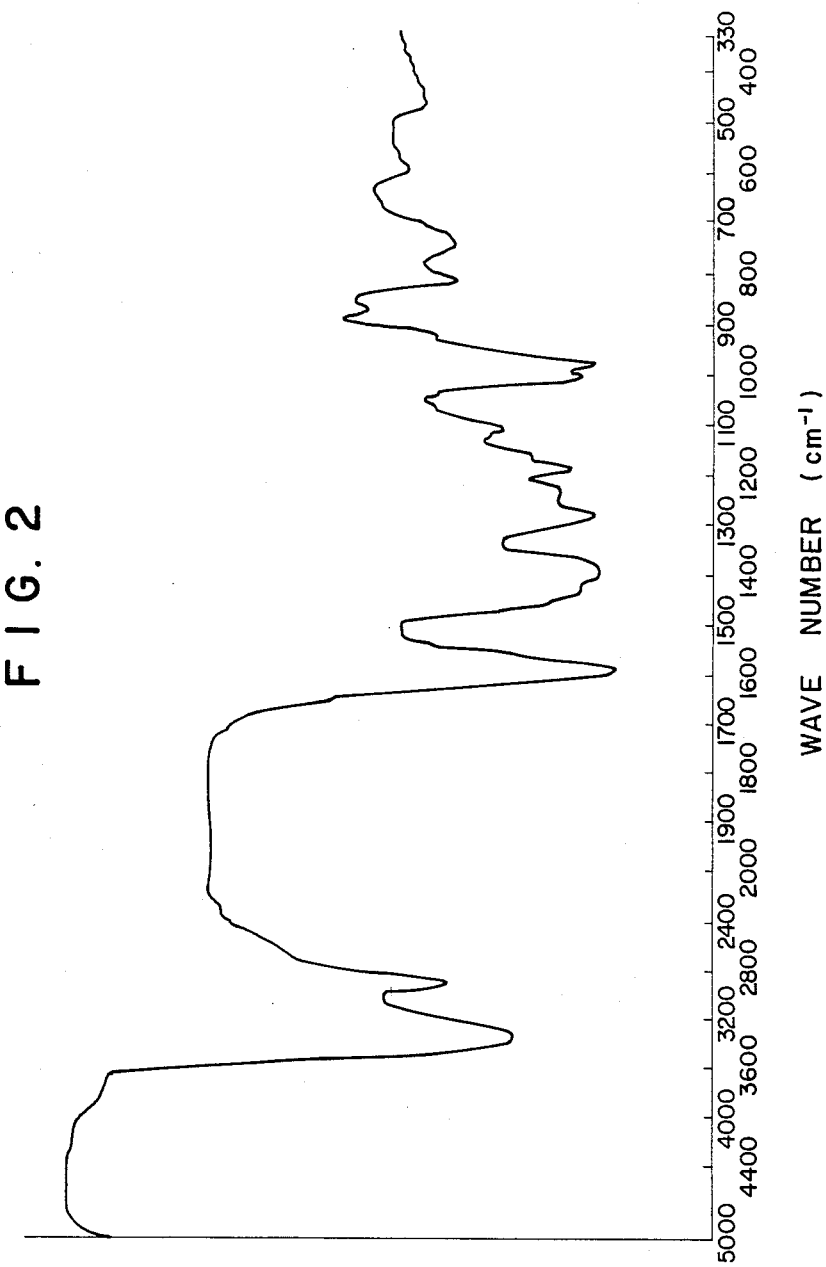
FIG. 2 is a graph showing the infrared absorption spectrum of R20X.
Figure 3:
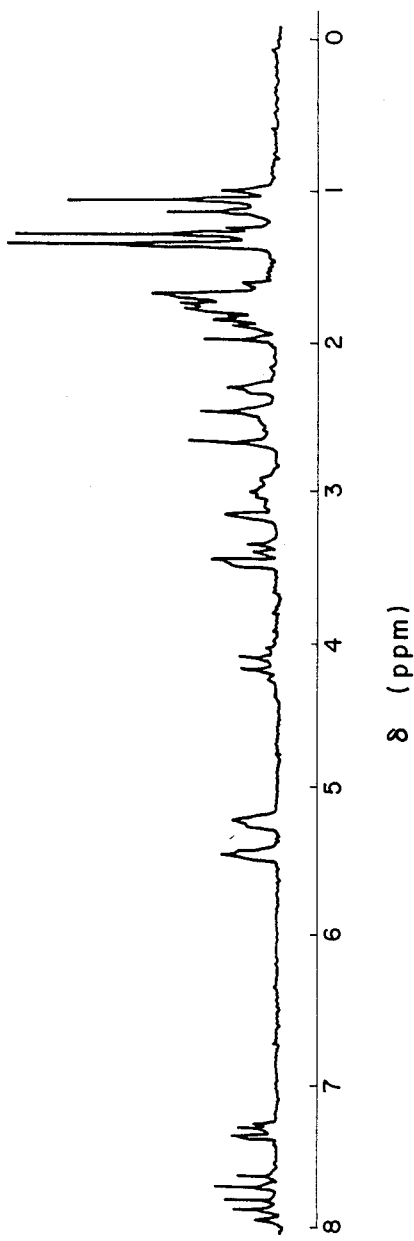
FIG. 3 is a graph showing the $^1$H-NMR spectrum of R20X.
Figure 4:
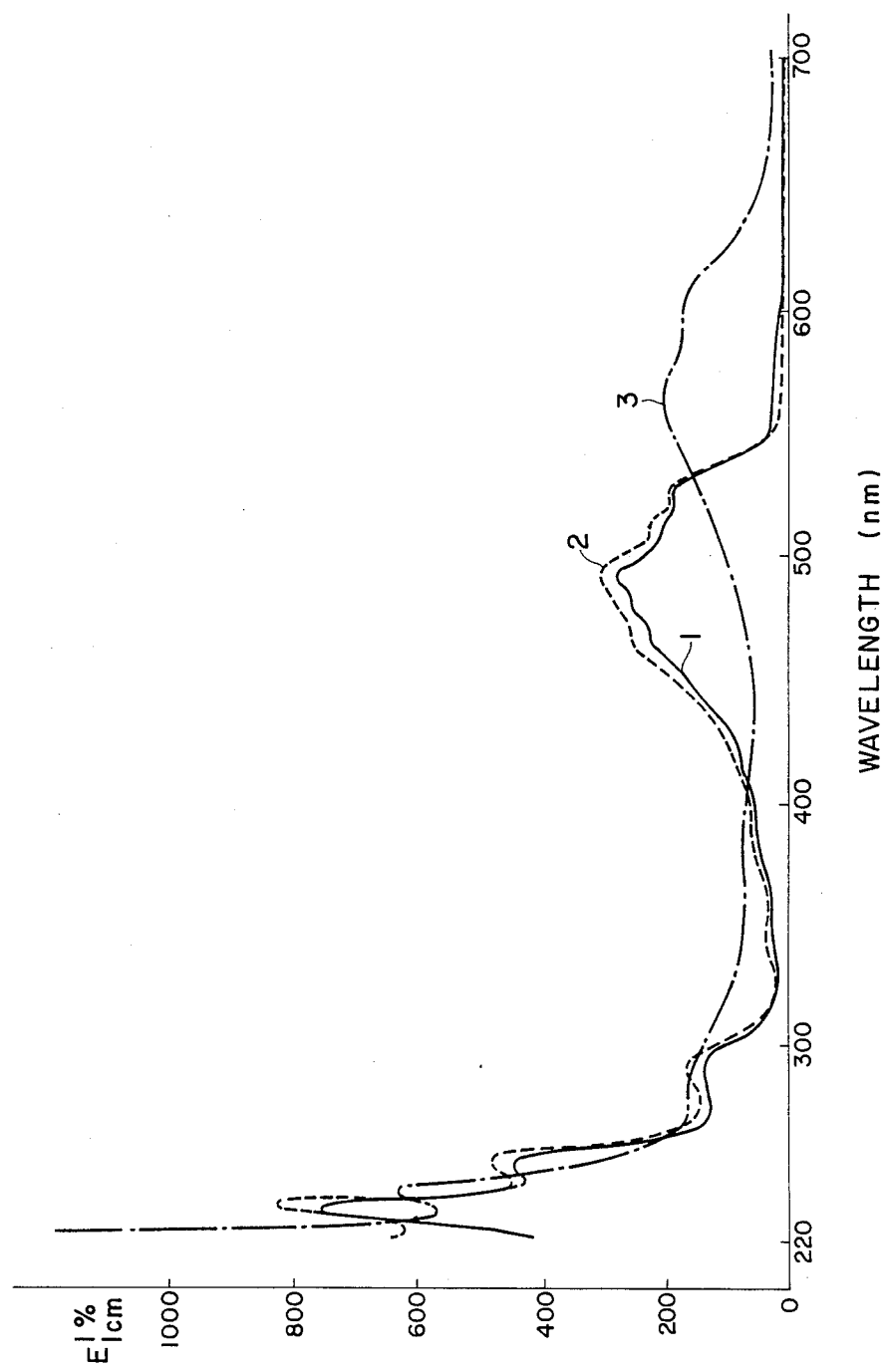
FIG. 4 is a graph indicating the ultraviolet and visible absorption spectra of R20X2, the curve 1 indicating the spectrum in MeOH, the curve 2 the spectrum in 0.1N HCl-MeOH, and the curve 3 the spectrum in 0.1N NaOH-MeOH.
Figure 5:
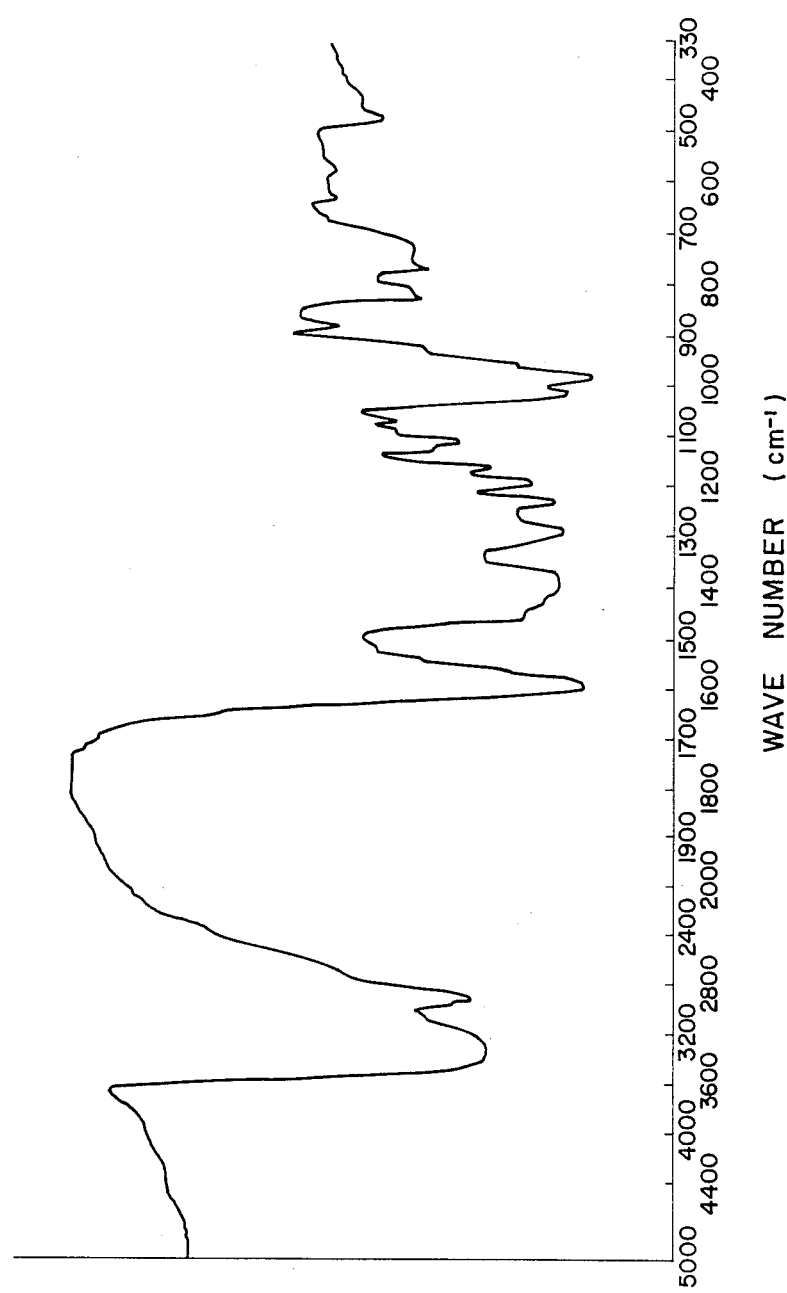
FIG. 5 is a graph indicating the infrared absorption spectrum of R20X2.
Figure 6:
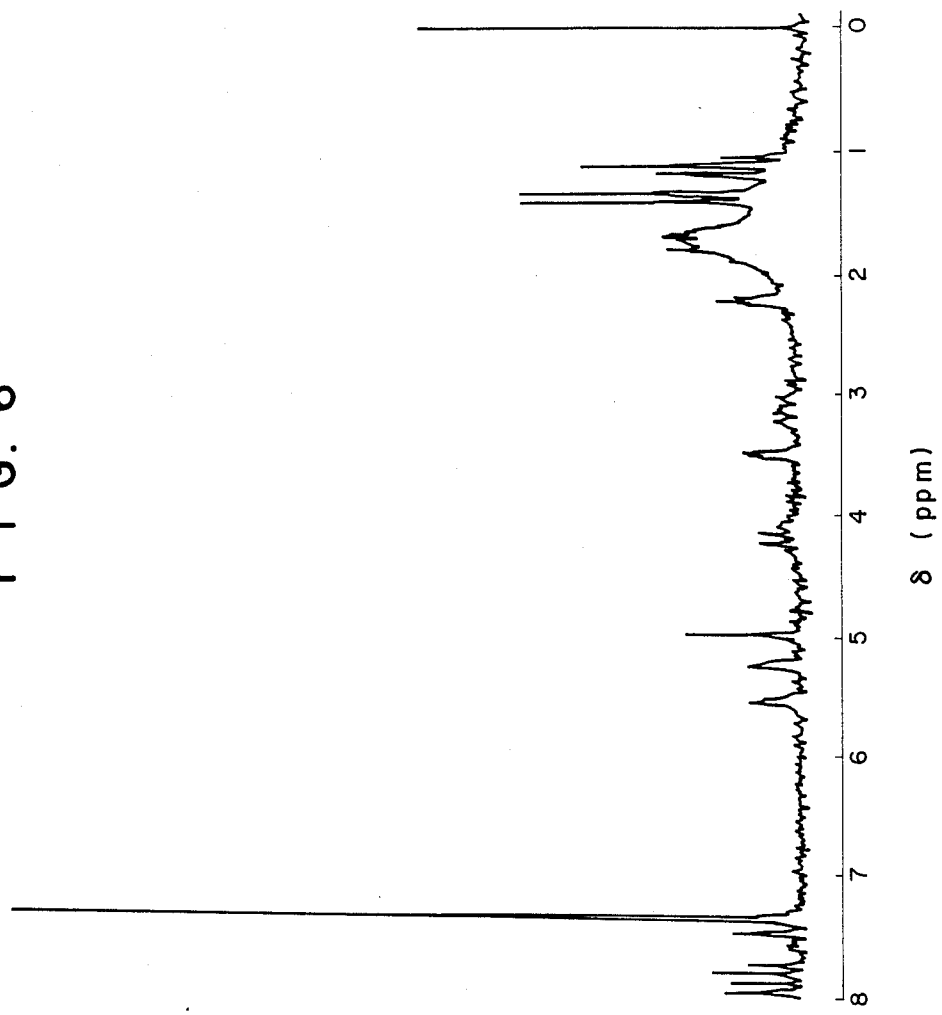
FIG. 6 is a graph showing the $^1$H-NMR spectrum of R20X2.

The physicochemical properties or physiological activities of the R20X, R20X2, M-R20X and M-R20X2 obtained in the above Reference Examples or Examples were as follows:

| No. | Properties | Physicochemical properties of R20X and R20X2 | | | | | | | |
|-----|-----------|---|---|---|---|---|---|---|---|
| | | R20X | | | | R20X2 | | | |
| 1 | Color & Form | Dark brown powder | | | | Dark brown powder | | | |
| 2 | Elemntary analysis (%) | C | H | N | O | C | H | N | Q |
| | Found | 61.83 | 5.99 | 2.76 | 29.42 | 60.45 | 5.77 | 2.66 | 31.12 |
| | Calcd. | 62.52 | 5.85 | 2.80 | 28.83 | 60.58 | 5.67 | 2.72 | 31.03 |
| 3 | Molecular weight | 499.5 | | | | 515.5 | | | |
| 4 | Melting point (°C.) | 131–134 (decomposed) | | | | 112–115 | | | |
| 5 | Specific rotatory power $[\alpha]_D^{25}$ | +258° (C = 0.05, in methanol) | | | | +263° (C = 0.1, in 1:1 chloroform-methanol) | | | |
| 6 | UV & visible absorption spectrum | FIG. 1 | | | | FIG. 4 | | | |
| 7 | IR absorption spectrum (KBr tablet) | FIG. 2 | | | | FIG. 5 | | | |
| 8 | Proton NMR spectrum (100 MHz, in deuterochloroform) | FIG. 3 | | | | FIG. 6 | | | |
| 9 | Solubility | soluble: acidic water, basic water, methanol, ethanol, propanol, acetone, ethyl acetate, chloroform Insoluble: water, hexane, cyclohexane, diethyl ether, petroleum ether | | | | Soluble: acidic water, basic water, methanol, ethanol, n-propanol, acetone, ethyl acetate, chloroform Insoluble: water, hexane, cyclohexane, diethyl ether, petroleum ether | | | |
| 10 | Rf value (on silica gel plate 60F$_{254}$, Merck & Co., Inc.) | 0.24 chloroform: methanol: water = 8:2:0.05/ 0.33 chloroform: methanol: acetic acid = 8:2:0.05/ 0.46 chloroform: methanol: aqueous ammonia = 8:2:0.05/ 10:1:1 | | | | 0.16 chloroform: methanol: water = 8:2:0.5/ 0.26 chloroform: methanol: acetic acid = *:2:0.05/ 0.44 chloroform: methanol: aqueous ammonia = 8:2:0.05/ 10:1:1 | | | |

Physicochemical properties and principal physiological activities

A. Physicochemical properties a. M-R20X (1) Appearance: Reddish brown powder
(2) Elementary analysis:

| | C | H | N | O |
|---|---|---|---|---|
| Found (%) | 62.98 | 6.31 | 2.40 | 28.31 |
| Calcd. (%) | 63.26 | 6.19 | 2.46 | 28.09 |

Figure 7:
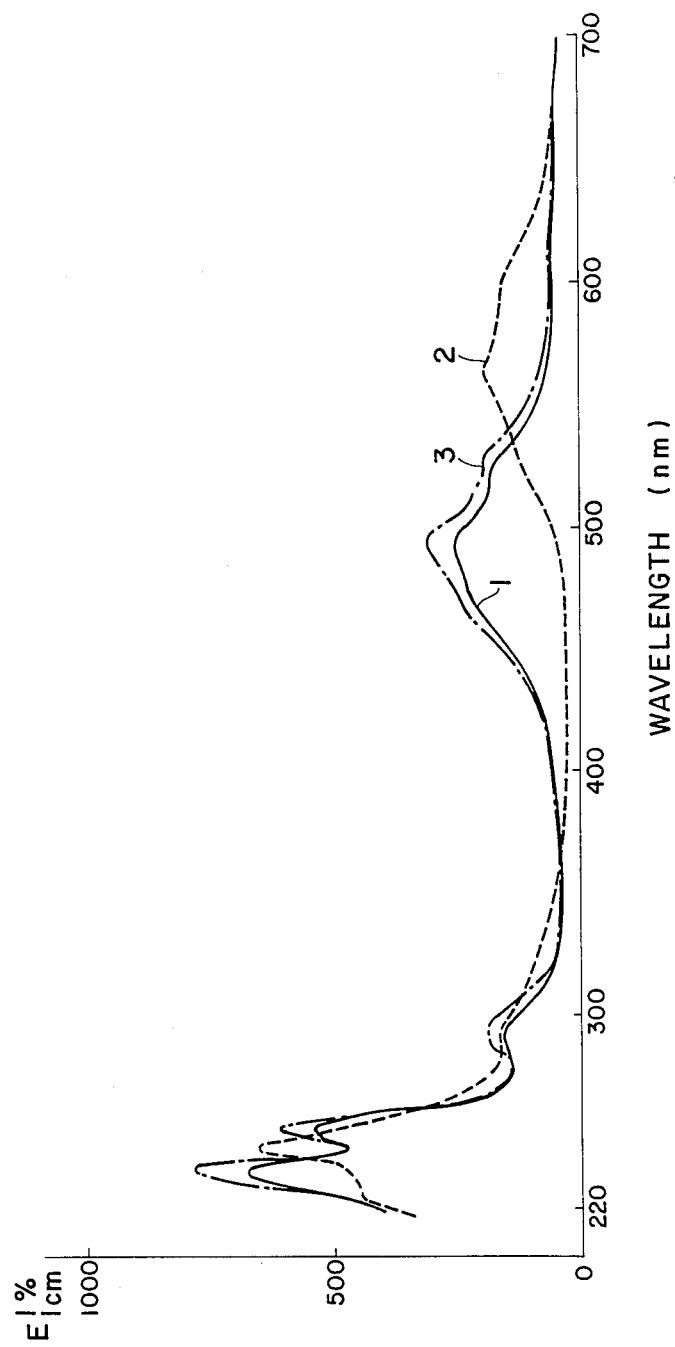
FIG. 7 is a graph showing the ultraviolet and visible absorption spectra of M-R20X, the curve 1 showing the spectrum in MeOH, the curve 2 the spectrum in 1N HCl-MeOH, and the curve 3 the spectrum in 0.1N NaOH-MeOH.
Figure 8:
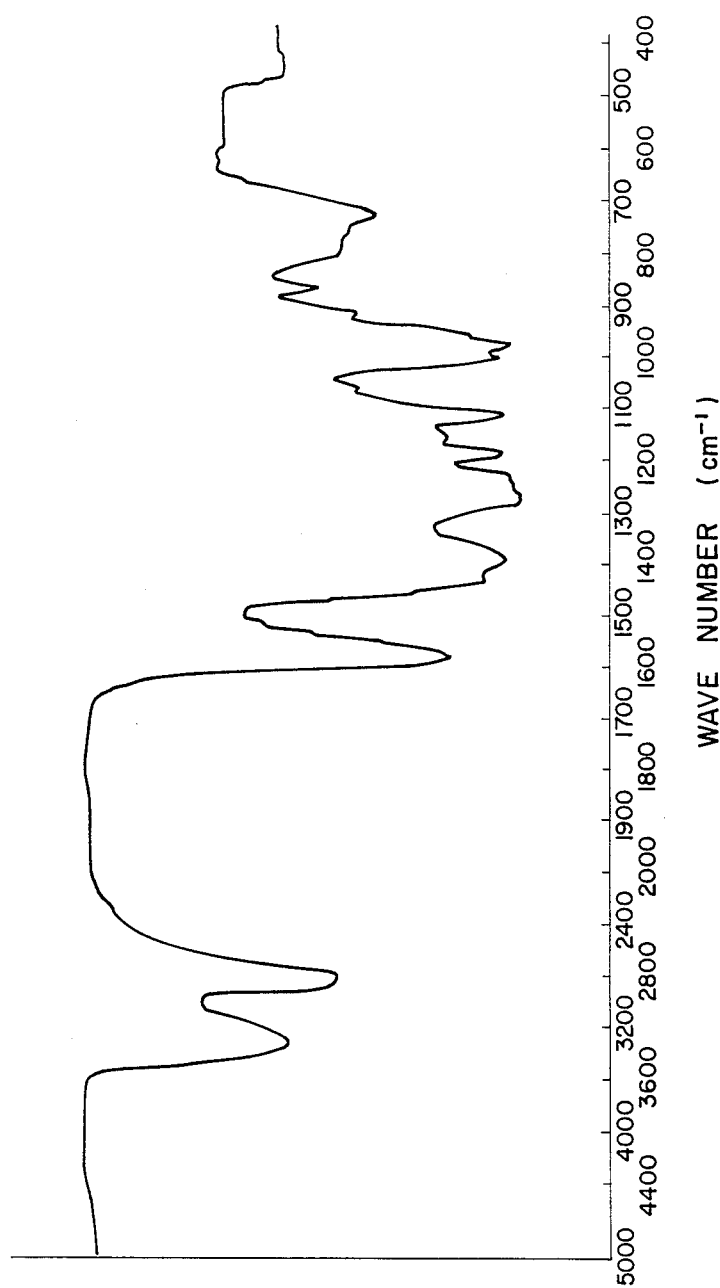
FIG. 8 is a graph showing the infrared absorption spectrum of M-R20X.
Figure 9:
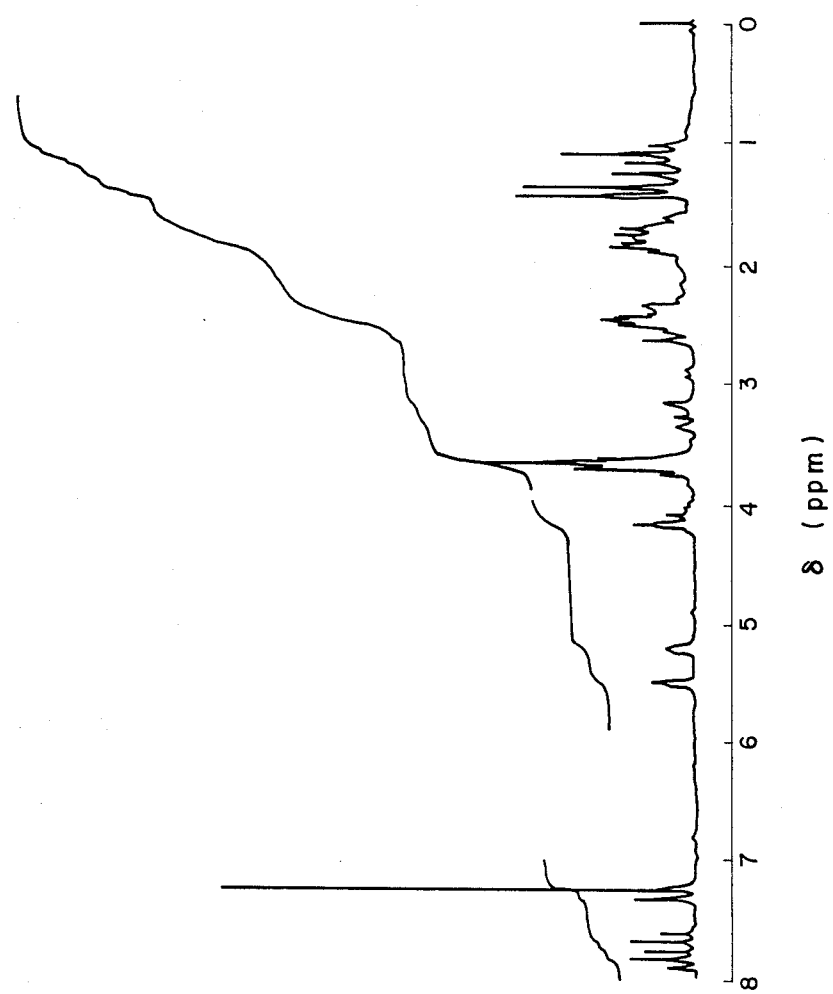
FIG. 9 is a graph showing the $^1$H-NMR spectrum of M-R20X.

(3) Molecular weight: 569.6
(4) Melting point: 143°–144° C. (decomposed)
(5) Specific rotatory power:
$[\alpha]_D^{25} = +76°$
(C=0.05, in methanol)
(6) Ultraviolet and visible absorption spectrum: As shown in FIG. 7.
  (a) in methanol $\lambda_{max}$ nm (E$_1$ $_{cm}$$^{1\%}$) 234 (683), 252 (545), 292 (158), 464 (205), 492 (261), 508 (194), 524 (181), 575 (18)
  (b) in acidic methanol $\lambda_{max}$ nm (E$_1$ $_{cm}$$^{1\%}$) 234 (783), 252 (612), 292 (192), 466 (233), 492 (315), 510 (227), 524 (202)
  (c) in alkaline methanol $\lambda_{max}$ nm (E$_1$ $_{cm}$$^{1\%}$) 226 (422), 243 (653), 290 (166), 528 (126), 562 (192), 596 (162)
(7) Infrared absorption spectrum (potassium bromide tablet): As shown in FIG. 8.
(8) Proton NMR spectrum: (100 MHz, in deuterochloroform) As shown in FIG. 9.
(9) Rf Value (on silica gel plate 60F$_{254}$, Merck & Co., Inc.)

| Developer | Rf Value |
|---|---|
| Chloroform:Methanol 10:1 | 0.42 |
| Chloroform:Methanol:Acetic acid 10:1:1 | 0.61 |
| Chloroform:Methanol:Triethylamine | 0.72 |

(10) Solubility: Soluble in acidic water, basic water, methanol, ethanol, propanol, acetone, ethyl acetate, and chloroform. Insoluble in water, hexane, cyclohexane, diethyl ether, and petroleum ether.

b. M-R20X2

(1) Appearance: Brown powder
(2) Elementary analysis:

| | C | H | N | O |
|---|---|---|---|---|
| Found (%) | 61.32 | 6.30 | 2.26 | 30.12 |
| Calcd. (%) | 61.53 | 6.02 | 2.39 | 30.06 |

Figure 10:
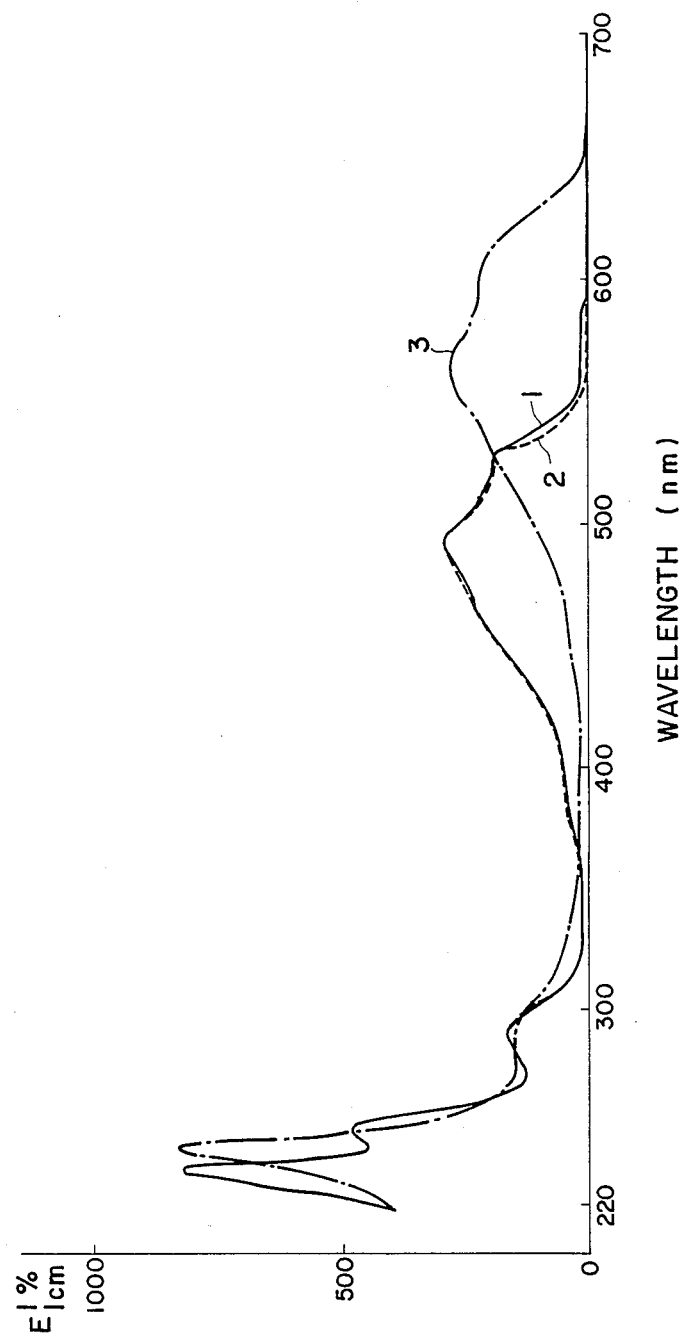
FIG. 10 is a graph illustrating the ultraviolet and visible absorption spectra of M-R20X2, the curve 1 showing the spectrum in MeOH, the curve 2 the spectrum in 0.1N HCl-MeOH, and the curve 3 the spectrum in 0.1N NaOH-MeOH.

(3) Molecular weight: 585.6
(4) Melting point: 155°–157° C. (decomposed)
(5) Ultraviolet and visible absorption spectrum: As shown in FIG. 10.
  (a) in methanol $\lambda_{max}$ nm (E$_1$ $_{cm}$$^{1\%}$) 234 (821), 252 (478), 290 (153), 468 (241), 480 (263), 492 (295), 514 (216), 526 (196), 582 (17)
  (b) in acidic methanol $\lambda_{max}$ nm (E$_1$ $_{cm}$$^{1\%}$) 234 (805), 252 (479), 290 (155), 468 (246), 480 (273), 492 (297), 512 (214), 526 (193), (c) in alkaline methanol $\lambda_{max}$ nm ($E_{1\ cm}^{1\%}$) 242 (831), 292 (149), 534 (212), 564 (280), 600 (226)

(6) Specific rotatory power:
$[\alpha]_D^{20} = +306°$
(C=0.05, in chloroform)

Figure 11:
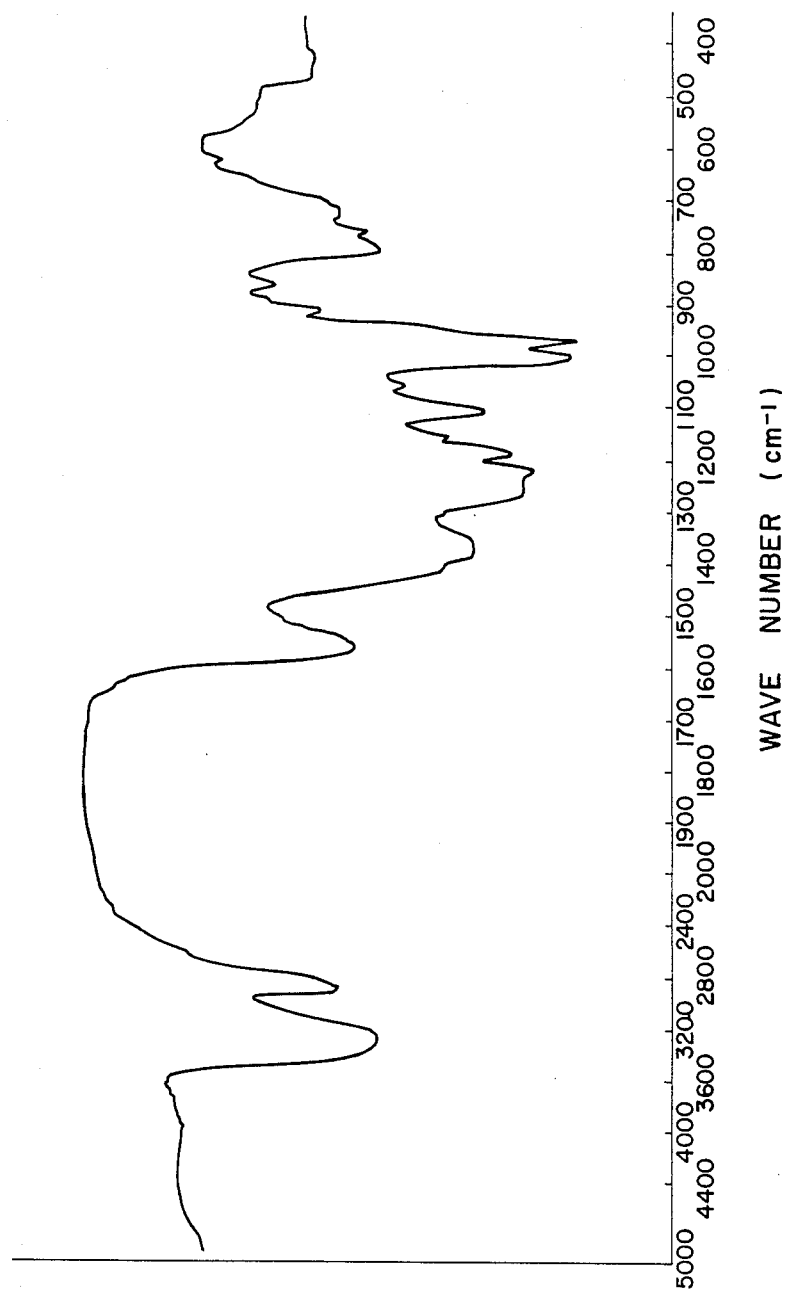
FIG. 11 is a graph showing the infrared absorption spectrum of M-R20X2.

(7) Infrared absorption spectrum (potassium bromide tablet): As shown in FIG. 11.

Figure 12:
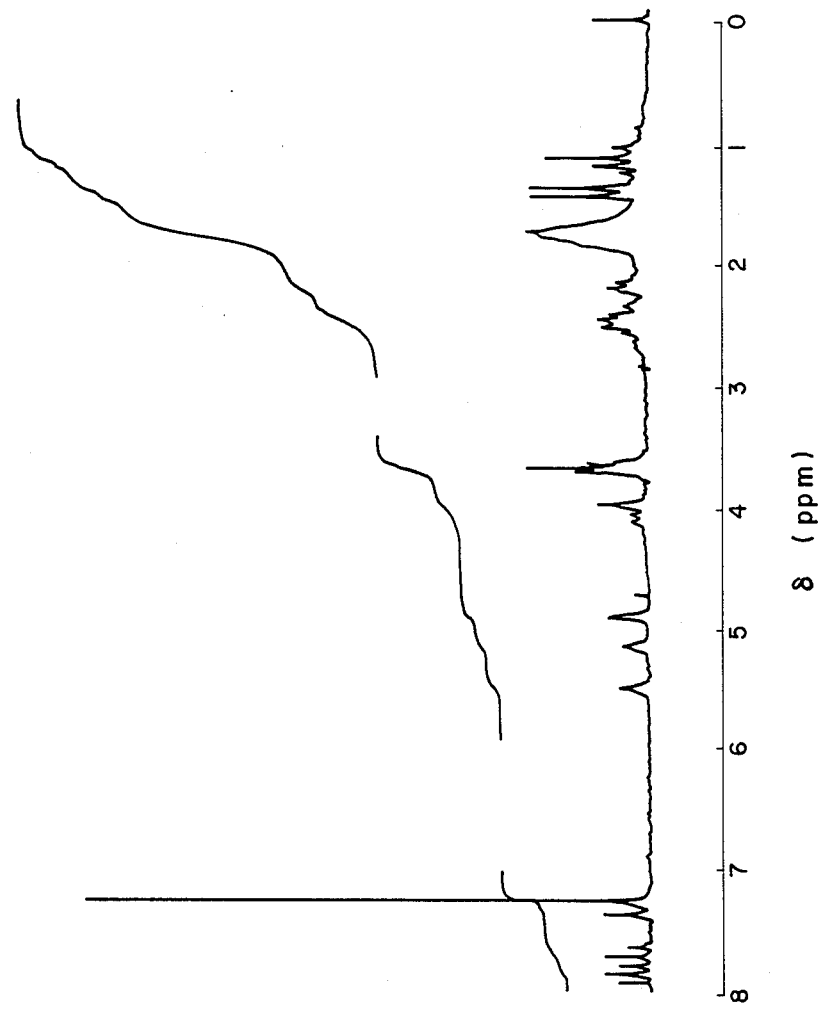
FIG. 12 is a graph indicating the $^1$H-NMR spectrum of M-R20X2.

(8) Proton NMR spectrum: (100 MHz, in deuterochloroform) As shown in FIG. 12.

(9) Solubility: Soluble in acidic water, basic water, methanol, ethanol, propanol, acetone, ethyl acetate, and chloroform. Insoluble in water, hexane, cyclohexane, diethyl ether, and petroleum ether.

(10) Rf Value (on silica gel plate 60F$_{254}$, Merck & Co., Inc.):

| Developer | Rf Value |
|---|---|
| Chloroform:Methanol 10:1 | 0.40 |
| Chloroform:Methanol:Acetic acid 10:1:1 | 0.59 |
| Chloroform:Methanol:Triethylamine 10:1:1 | 0.72 |

B. Physiological activities a. Antitumor activity

Into CDF$_1$ mice were intraperitoneally transplanted P388 leukemia 1×10$^6$ cells/mouse as a suspension, and M-R20X or M-R20X2 was administered to the mice intravenously 1 day and 5 days respectively after the transplantation. The mice were observed for 30 days, and the effect of the compounds evaluated in terms of the increase in life span (%) of the test mice as determined by specifying the survival days of the control mice to which was administered physiological saline solution as 100% was as shown in the following Table. Also presented are therapeutic indices of the compounds.

Increase in life span and therapeutic index in the case of i.v. administration

| | | Compound | | |
|---|---|---|---|---|
| Dose (mg/kg/day) | | M-R20X | M-R20X2 | Adriamycin (Comp. data) | Aclacinomycin (Comp. data) |
| Increase in life span T/C (%) | 0.25 | — | 109 | — | — |
| | 0.5 | — | 136 | — | — |
| | 1 | 104 | 154 | 103 | — |
| | 2 | 119 | 204 | 119 | — |
| | 4 | 155 | 194 | 133 | 121 |
| | 8 | 151 | 35* | 165 | 119 |
| | 12 | 57 | — | 224 | — |
| | 16 | — | — | — | 151 |
| | 32 | — | — | — | 177 |
| | 64 | — | — | — | 35* |
| Dose for T/C = 130% (mg/kg/day) | | 2.5 | 0.43 | 3.5 | 12.4 |
| Therapeutic index | | 1.6 | 4.7 | 3.4 | 2.6 |

*administered only day 1 b. Acute toxicity (LD$_{50}$ values)

LD$_{50}$ values of M-R20X and M-R20X2 administered to ICR mice by intravenous injection were as shown below:

| Drug | LD$_{50}$(mg/kg) |
|---|---|
| M-R20X | 12.3 |
| M-R20X2 | 3.55 |

What is claimed is:

1. A process for producing a 10-hydroxyanthracycline of the following formula (II)

which consists of reacting a compound of the following formula (I)

or an acid addition salt thereof with an N-oxide of a tertiary amine wherein R$^1$ through R$^6$ are selected from the group consisting of H, OH and OCH$_3$; R$^7$ is selected from the group consisting of H, OH,

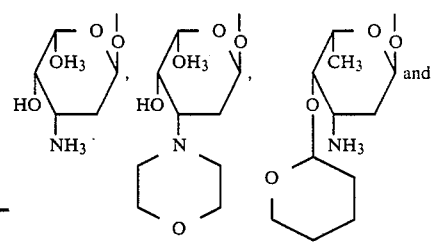

and

-continued

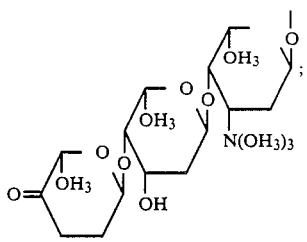

and $R^8$ is selected from the group consisting of $C_2H_5$, $COCH_3$, $CH(OH)CH_3$, $CH(OH)CH_2(OH)$ and $COCH_2OH$.

2. The process as in claim 1 wherein the reaction is carried out in a solvent selected from the group consisting of dimethylformamide, acetonitrile, acetone, and dimethyl sulfoxide.

3. The process, as in claim 2 wherein the reaction is carried out at a temperature in the range of the solidifying point to the boiling point of the solvent.

4. The process, as in claim 3 wherein the reaction occurs from several hours to several days.

5. The process, as in claim 1 wherein the acid addition salts of the compound of formula (I) are selected from the group consisting of inorganic salts of hydrochloric acid, sulfuric acid, phosphoric acid, organic salts of acetic acid, lactic acid, propionic acid, maleic acid, oleic acid, palmitic acid, citric acid, succinic acid, tartaric acid, fumaric acid, glutamic acid, pantothenic acid and laurylsulfonic acid.

6. The process, as in claim 1 wherein the N-oxide of a tertiary amine is selected from the group consisting of trimethylamine N-oxide, triethylamine N-oxide, N-methylmorpholin-N-oxide and hydrates thereof.

7. The process, as in claim 1 wherein the compounds of formula I are selected from the group consisting of adriamycin, daunomycin, aclacinomycin, THF-adriamycin, carminomycin, 3'deamino-3'-(4-morpholinyl)-13-deoxocarmincinycin and acid addition salts thereof.

* * * * *

UNITED STATES PATENT AND TRADEMARK OFFICE
CERTIFICATE OF CORRECTION

PATENT NO. : 4,877,870

DATED : October 31, 1989

INVENTOR(S) : Hamao UMEZAWA ET AL

It is certified that error appears in the above-identified patent and that said Letters Patent is hereby corrected as shown below:

In col.7, line 63 delete "$(E_1{cm1\%})$" and add -- $(E^{1\%}_{1cm})$ --.

In col.7, line 66 delete "$(E_{1cm}^{1\%})$" and add -- $(E^{1\%}_{1cm})$ --

In col.8, line 1 delete "$(E_{1cm}^{1\%})$" and add -- $(E^{1\%}_{1cm})$ --

In col.8, line 17 the ratio and underline there below have been omitted, change chart to

| Developer | Rf Value |
|---|---|
| Chloroform:Methanol 10:1 | 0.42 |
| Chloroform:Methanol:Acetic Acid 10:1:1 | 0.61 |
| Chloroform:Methanol:Triethylamine 10:1:1 | 0.72 |

In col.8, line 40 delete "=*:2:0.05/" and add -- =8:2:0.0 5/--

In col.8, line 44 erase the ratio "10:1"1" and the line there below

In col.8, line 63 delete "$(E_{1cm}^{1\%})$" and add -- $(E^{1\%}_{1cm})$ --

In col.8, line 66 delete "$(E_{1cm}^{1\%})$" and add -- $(E^{1\%}_{1cm})$ --

In col.9, line 1 delete "$(E_{1cm}^{1\%})$ and add -- $(E^{1\%}_{1cm})$ --

UNITED STATES PATENT AND TRADEMARK OFFICE
CERTIFICATE OF CORRECTION

PATENT NO. : 4,877,870

DATED : October 31, 1989

INVENTOR(S) : Hamao UMEZAWA ET AL

It is certified that error appears in the above-identified patent and that said Letters Patent is hereby corrected as shown below:

Col 10, claim 1, lines 36-43 delete the formulas shown therein and replace therefore.

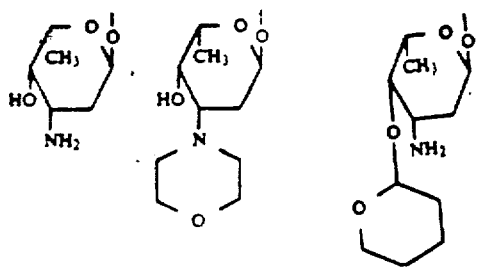

UNITED STATES PATENT AND TRADEMARK OFFICE
CERTIFICATE OF CORRECTION

PATENT NO. : 4,877,870

DATED : October 31, 1989

INVENTOR(S) : Hamao Umezawa, et al

It is certified that error appears in the above-identified patent and that said Letters Patent is hereby corrected as shown below:

Col. 11, claim 1, lines 4-12, delete the formula shown therein and replace therefore

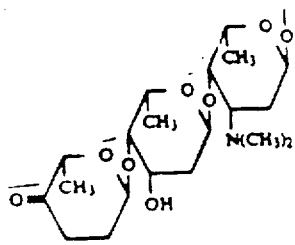

Signed and Sealed this

Tenth Day of September, 1991

Attest:

HARRY F. MANBECK, JR.

Attesting Officer

Commissioner of Patents and Trademarks